United States Patent
Hutton et al.

(10) Patent No.: US 8,882,661 B2
(45) Date of Patent: Nov. 11, 2014

(54) RETRACTOR

(75) Inventors: Clark Hutton, San Clemente, CA (US); Thomas Purcell, Del Mar, CA (US); Christopher M. Campbell, Temecula, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 976 days.

(21) Appl. No.: 11/903,896

(22) Filed: Sep. 24, 2007

(65) Prior Publication Data

US 2008/0114208 A1    May 15, 2008

Related U.S. Application Data

(60) Provisional application No. 60/846,476, filed on Sep. 22, 2006.

(51) Int. Cl.
  *A61B 1/32*  (2006.01)
  *A61B 17/02*  (2006.01)

(52) U.S. Cl.
  CPC ............ *A61B 17/02* (2013.01); *A61B 17/0293* (2013.01); *A61B 17/0206* (2013.01)
  USPC ............ 600/201; 600/224; 600/231; 600/232

(58) Field of Classification Search
  USPC ................................. 600/201–246
  See application file for complete search history.

(56) References Cited

U.S. PATENT DOCUMENTS

| | | | |
|---|---|---|---|
| 5,520,610 A * | 5/1996 | Giglio et al. ................. | 600/233 |
| 5,728,046 A * | 3/1998 | Mayer et al. ................. | 600/210 |
| 5,944,658 A * | 8/1999 | Koros et al. .................. | 600/232 |
| 8,038,611 B2 * | 10/2011 | Raymond et al. ............ | 600/231 |
| 2004/0002629 A1 | 1/2004 | Branch et al. | |
| 2006/0084844 A1* | 4/2006 | Nehls ........................... | 600/227 |
| 2006/0224044 A1* | 10/2006 | Marchek et al. ............. | 600/233 |
| 2007/0156024 A1* | 7/2007 | Frasier et al. ................ | 600/219 |
| 2007/0156026 A1 | 7/2007 | Frasier et al. | |
| 2007/0208228 A1 | 9/2007 | Pavento et al. | |

FOREIGN PATENT DOCUMENTS

| | | |
|---|---|---|
| WO | WO 2005/060837 A2 | 7/2005 |
| WO | WO 2005/094695 A2 | 10/2005 |
| WO | WO 2007/087536 A2 | 8/2007 |
| WO | WO 2007/103997 A2 | 9/2007 |

OTHER PUBLICATIONS

International Search Report for Application No. PCT/US2007/020625 dated of mailing Jul. 3, 2008.

* cited by examiner

*Primary Examiner* — Pedro Philogene
*Assistant Examiner* — Christina Negrellirodrigue
(74) *Attorney, Agent, or Firm* — Michael J. Loi

(57) ABSTRACT

A retractor device for spearing the body tissue apart is provided. The retractor includes a housing configured to include a plurality of sections, wherein each section is configured to accommodate placement of at least one blade, a blade holding mechanism configured to secure the at least one blade within the housing, a translation mechanism configured to provide translation movement of at least one of the sections, and a rotation mechanism configured to provide rotation movement of at least one blade.

17 Claims, 19 Drawing Sheets

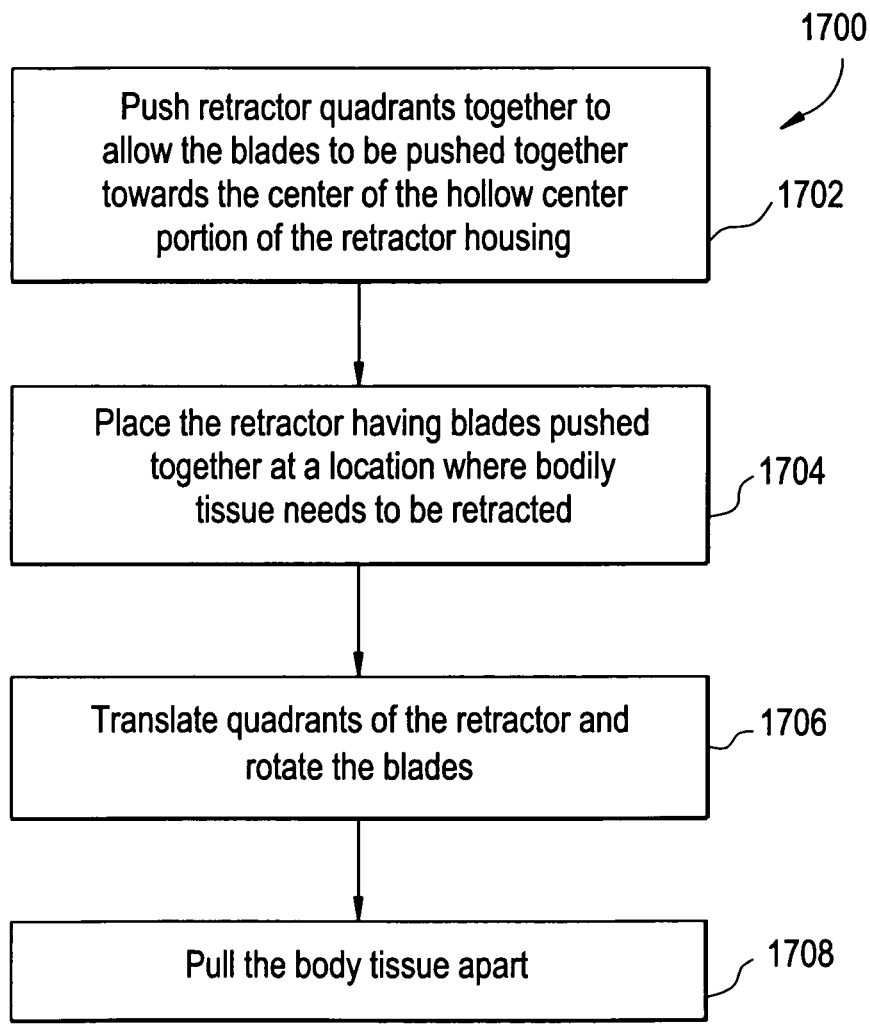

RETRACTOR

CROSS-REFERENCE TO RELATED APPLICATIONS

The present application claims priority to U.S. Provisional Patent Application No. 60/846,476 to Hutton et al., filed Sep. 22, 2006, and entitled "Retractor", and incorporates its subject matter herein by reference in its entirety.

The present application also relates to U.S. patent application Ser. No. 11/544,890, filed Oct. 6, 2006, and entitled "Retractor and Methods of Use", which claims priority to U.S. Provisional Application No. 60/725,007, to Hutton, filed Oct. 7, 2005, and titled "Retractor". The disclosures of these applications are incorporated herein by reference in their entireties.

BACKGROUND OF THE INVENTION

1. Field of the Invention

The present invention relates generally to the field of surgery, and more specifically, to a retractor device which may be used during spinal surgery for exposure of a surgical site.

2. Background of the Invention

There is a significant number of people that suffer spinal disorders that may require spinal surgery and/or intervention. Such surgeries typically require exposure and access to the internal spinal elements. Through the exposure, the surgeon may remove, add, medicate, and/or modify pathological elements to remedy the spinal disorder.

Conventional treatment may also include traction, either with a halter or with Crutchfield type tongs, followed by an application of a cast or a brace. If surgery is necessary, the area of injury is often fixed with a wire to allow fusion of the vertebrae in the affected region of the vertebral column. Often treatment also includes anterior decompression and fusion, or more recently, plates and screws to immobilize the unstable region. Such plates may be used either anteriorly or posteriorly, or in a few cases, both anteriorly and posteriorly.

In order to carry out such spinal surgery, the surgical area must be of sufficient size to allow the surgeon ample access for carrying out procedures. Many current devices do not permit a surgeon or other qualified professional easy access to a surgical site, and moreover, current devices do not address the clearing of tissue obstructions at deeper levels in the surgical site. Thus, there is a need for a device that can assist a surgeon or other qualified profession in retracting obstructive tissue away from the surgical site.

SUMMARY OF THE INVENTION

The present invention is directed to systems, methods, and devices applicable to spinal surgery. More specifically, the present invention is directed to a tissue retractor for use by medical personnel (i.e., doctor) in spinal and other surgical procedures.

In particular, embodiments of the present invention are useful in the performance of discectomy, laminectomy, intervertebral fusion, pedicle/facet/bone screw installation, and spondy reduction procedures (for example), and is especially useful in posterior approach applications.

In some embodiments, the present invention relates to a retractor. The retractor includes a housing configured to include a plurality of sections, wherein each section is configured to accommodate placement of at least one blade, a blade holding mechanism configured to secure the at least one blade within the housing, a translation mechanism configured to provide translation movement of at least one of the sections, and a rotation mechanism configured to provide rotation movement of at least one blade.

In some embodiments, the present invention relates to a method for retracting body tissue within a body of a patient using a retractor device. The retractor includes a housing with a center and configured to include a plurality of sections, wherein each section is configured to accommodate placement of at least one blade, a blade holding mechanism configured to secure the at least one blade within the housing, a translation mechanism configured to provide translation movement of at least one of the sections, and a rotation mechanism configured to provide rotation movement of at least one blade. The method includes steps of inserting the blades attached to the sections of the retractor into the body tissue selected for retraction, wherein the blades of the retractor have been previously pushed together, translating the sections of the retractor to a desired distance, wherein the translating translates the blades away from the center of the housing thereby spreading the body tissue apart, and rotating the blades in a plane substantially perpendicular to the plane of the translating to further push the body tissue apart.

BRIEF DESCRIPTION OF THE DRAWINGS

The present invention is described with reference to the accompanying drawings. In the drawings, like reference numbers indicate identical or functionally similar elements.

FIG. 17 is a flowchart illustrating method for retracting tissue at a surgical site using the retractor shown in FIG. 1.

DETAILED DESCRIPTION OF THE INVENTION

The present invention is directed to systems, methods, and devices applicable to spinal surgery. More specifically, the present invention is directed to a tissue retractor for use by medical personnel (i.e., doctor) in spinal and other surgical procedures.

In particular, embodiments of the present invention are useful in the performance of discectomy, laminectomy, intervertebral fusion, pedicle/facet/bone screw installation, and spondy reduction procedures (for example), and is especially useful in posterior approach applications.

As illustrated in FIGS. 1-16, some embodiments of the present invention are directed to a four-quadrant retractor having a plurality of blades, including (for example), a medial blade, a lateral blade, a cephlal blade, and a caudal blade. In some embodiments, the retractor may also include an expansion mechanism and a blade holding/retention mechanism. In such embodiments, the blades can be removed in-situ and replaced with longer or shorter blades if necessary. In some embodiments, if a fixed non-expandable port-hole configuration of the retractor is desired, the blades can be locked together with a top-loading nut/fastener. In an alternate embodiment, the retractor may also include a worm and gear drive for accomplishing distal toeing of the blades. Such a drive can articulate segments to which the blades are attached.

In some embodiments, the retractor includes one or more blade holding segments, which can be forced apart to allow for distraction of the construct. Additionally, the retractor may also include a ratchet mechanism to hold an "open" position (i.e., when blade holding segments are forced apart) for one or more blade holding segment relative to other blade holding segments.

In some embodiment, the retractor can include one or more accessory blades. The accessory blades may be installed after an initial retraction to hold back soft tissue, which sometimes encroaches into a surgical area.

Figure 1:
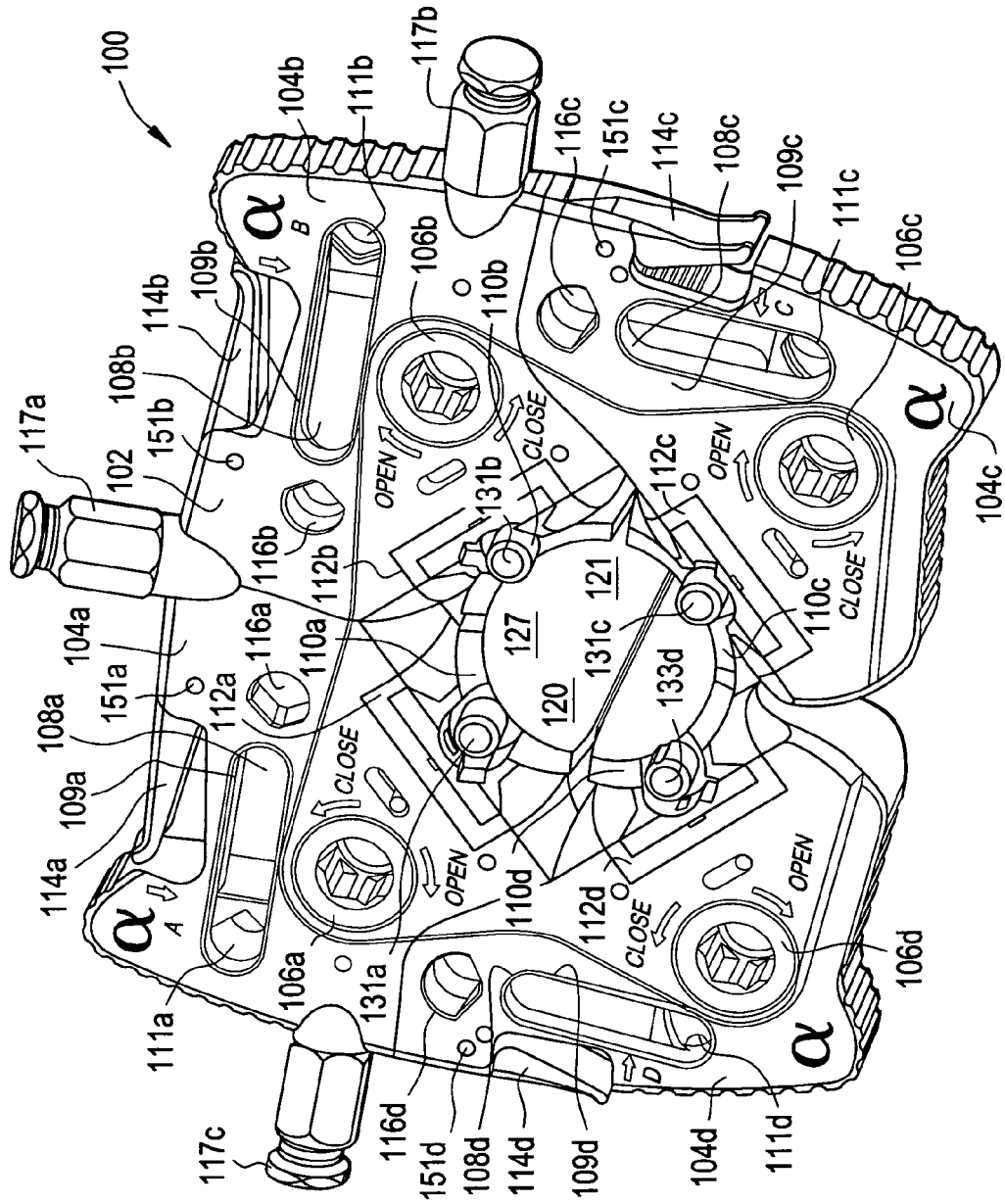
FIG. 1 is a perspective, cross-sectional view of a collapsed retractor, according to some embodiments of the present invention.
Figure 2:
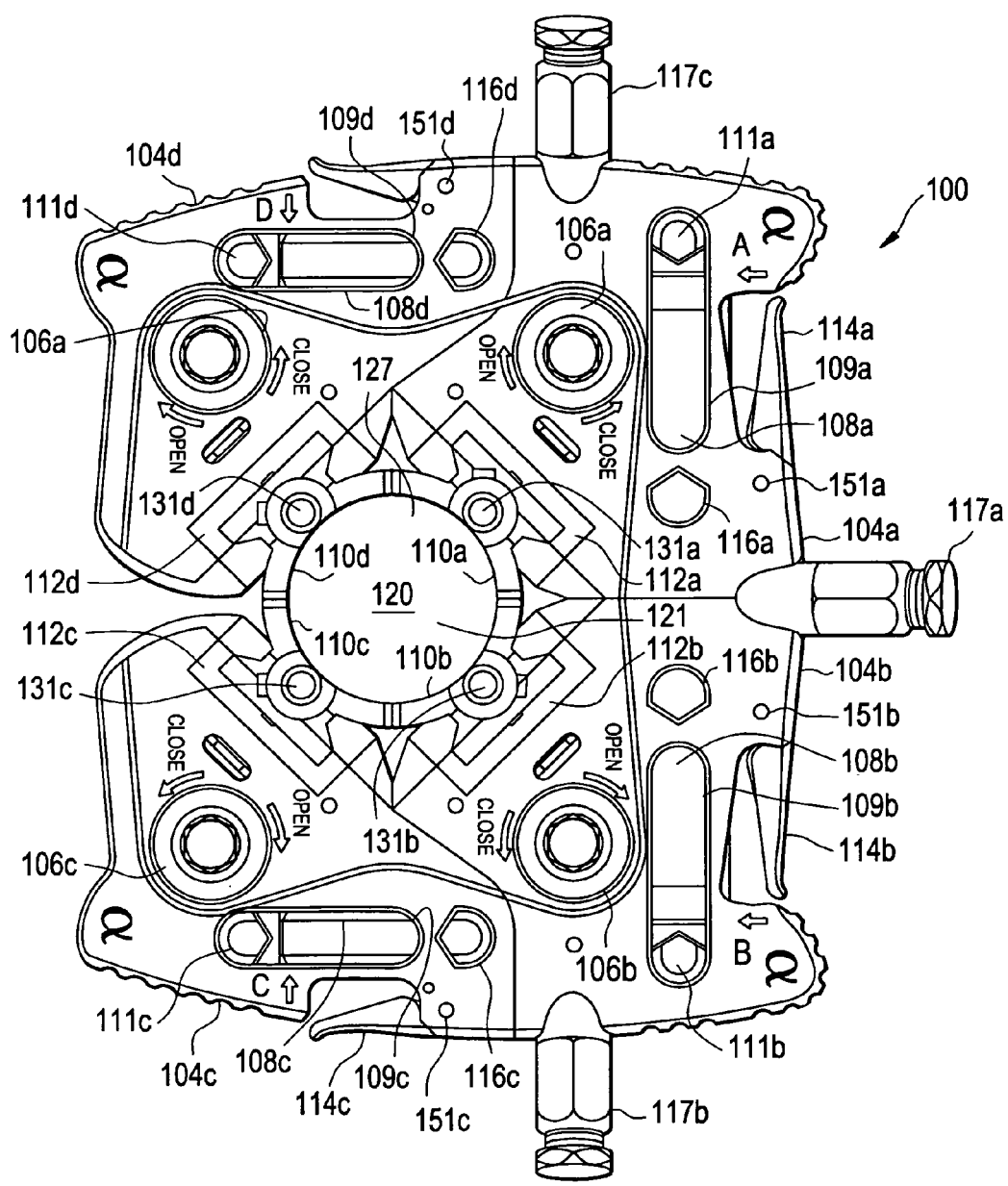
FIG. 2 is top view of the retractor device shown in FIG. 1.

FIG. 1 is a perspective view of a retractor 100, according to some embodiments of the present invention. The retractor 100 includes a housing 102 that is configured to include four quadrants (or sections) 104 (*a, b, c, d*). Each quadrant 104 (*a, b, c, d*) is configured to include a blade holder 112 (*a, b, c, d*), a gear drive 106 (*a, b, c, d*), a ratchet 114 (*a, b, c, d*), and a detractor assembly 109(*a, b, c, d*), respectively. The housing 102 is further configured to include a hollow interior 120 having a center 121. The hollow interior 120 is configured to be formed by the quadrants 104(*a, b, c, d*) and is configured to be enclosed by each respective quadrant 104. The center 121 is configured to be located substantially in the center of the hollow interior 120.

Figure 4:
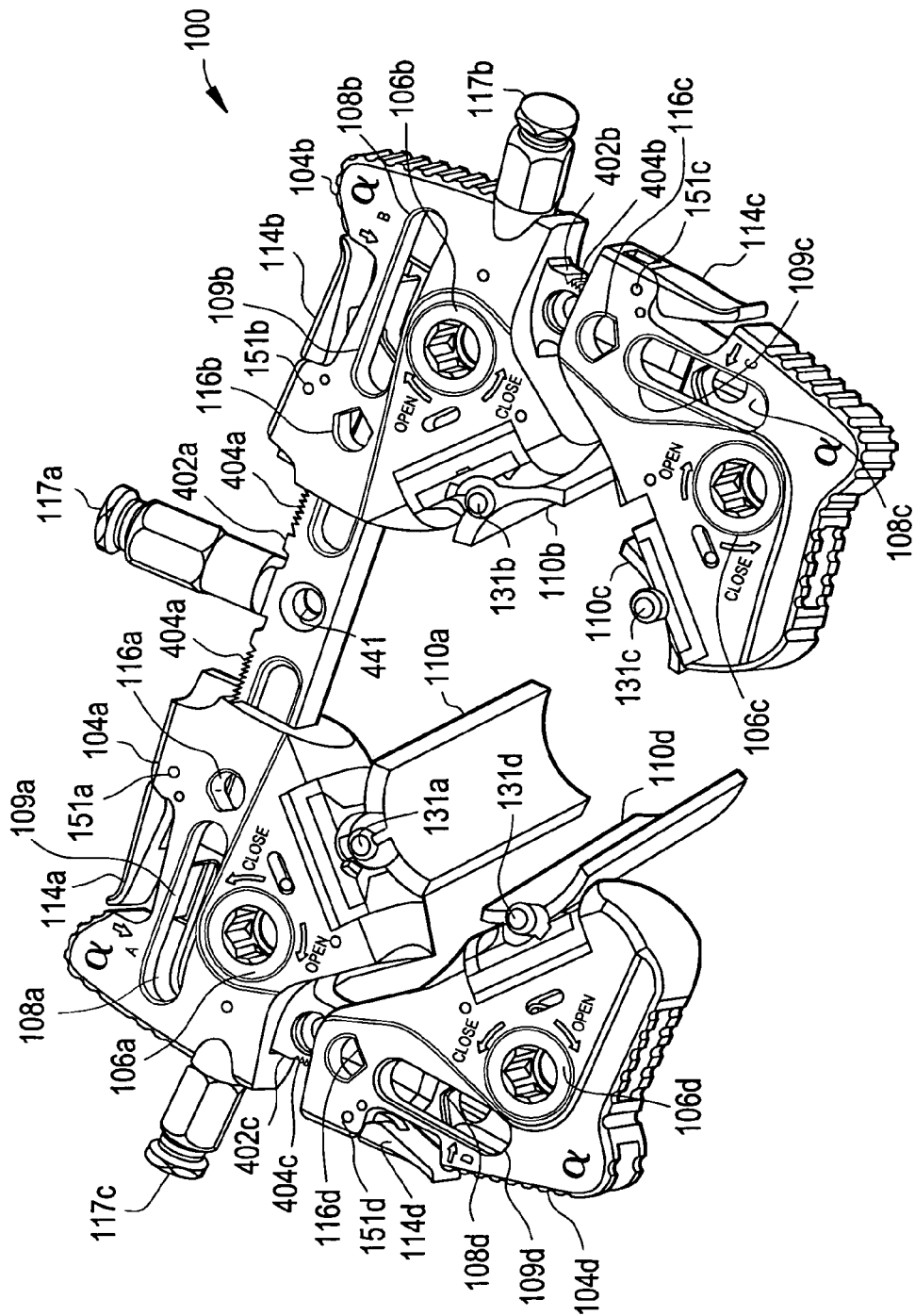
FIG. 4 is a perspective, cross-sectional view of an expanded retractor shown in FIG. 1.

The retractor 100 is configured to have at least two states: a collapsed (or unexpanded state) and an expanded state. In the collapsed state, the quadrants 104(*a, b, c, d*) are configured to be pulled together and are further configured to be adjacent to each other, as shown in FIG. 1. In the expanded state, the quadrants 104 (*a, b, c, d*) are configured to be pulled apart as shown in FIG. 4. As can be understood by one skilled in the art, in the expanded state, the quadrants 104 can be pulled apart to any distance from each other. This distance depends on an amount of tissue that needs to be pulled apart, size of the surgical site, and any other factors. In the expanded state, one quadrant can be pulled away while the other quadrants remain adjacent to each other. As can be further understood by one skilled in the art, in the expanded state any number of quadrants can be pulled apart. As such, expansion/contraction of each quadrant can be controlled independently of the other quadrants. Such control can be implemented using various tools that will be discussed below with reference to FIGS. 10-14.

The quadrants 104*a* and 104*b* are configured to be removably coupled together using a holder 117*a*. The quadrants 104*b* and 104*c* are configured to be removably coupled together using a holder 117*b*. The quadrants 104*a* and 104*d* are configured to be removably coupled using a holder 117*c*. The quadrants 104*c* and 104*d* are configured to be adjacent to each other when the retractor 100 is in a collapsed (or unexpanded) state. The holders 117 can be configured to secure four quadrants and prevent the retractor 100 from falling apart. The holders 117 can be also configured to secure the retractor 100 to the surgical table (not shown in FIG. 1). Alternatively, the retractor 100 can be secured to the surgical table or any other surface using a rigid, flexible, or semi-rigid, semi-flexible arm.

Each quadrant 104 is further configured to be slidably coupled to one another (except that in some embodiments quadrants 104*c* and 104*d* are not slidably coupled to each other). Thus, quadrants 104 are capable of translational movement within the same plane as the housing 102. As the quadrants 104 include blades 110 (*a, b, c, d*), translational movement of the quadrants 104 causes translational movement of the blades 110 in the plane parallel to the plane of the housing 102.

Figure 15:
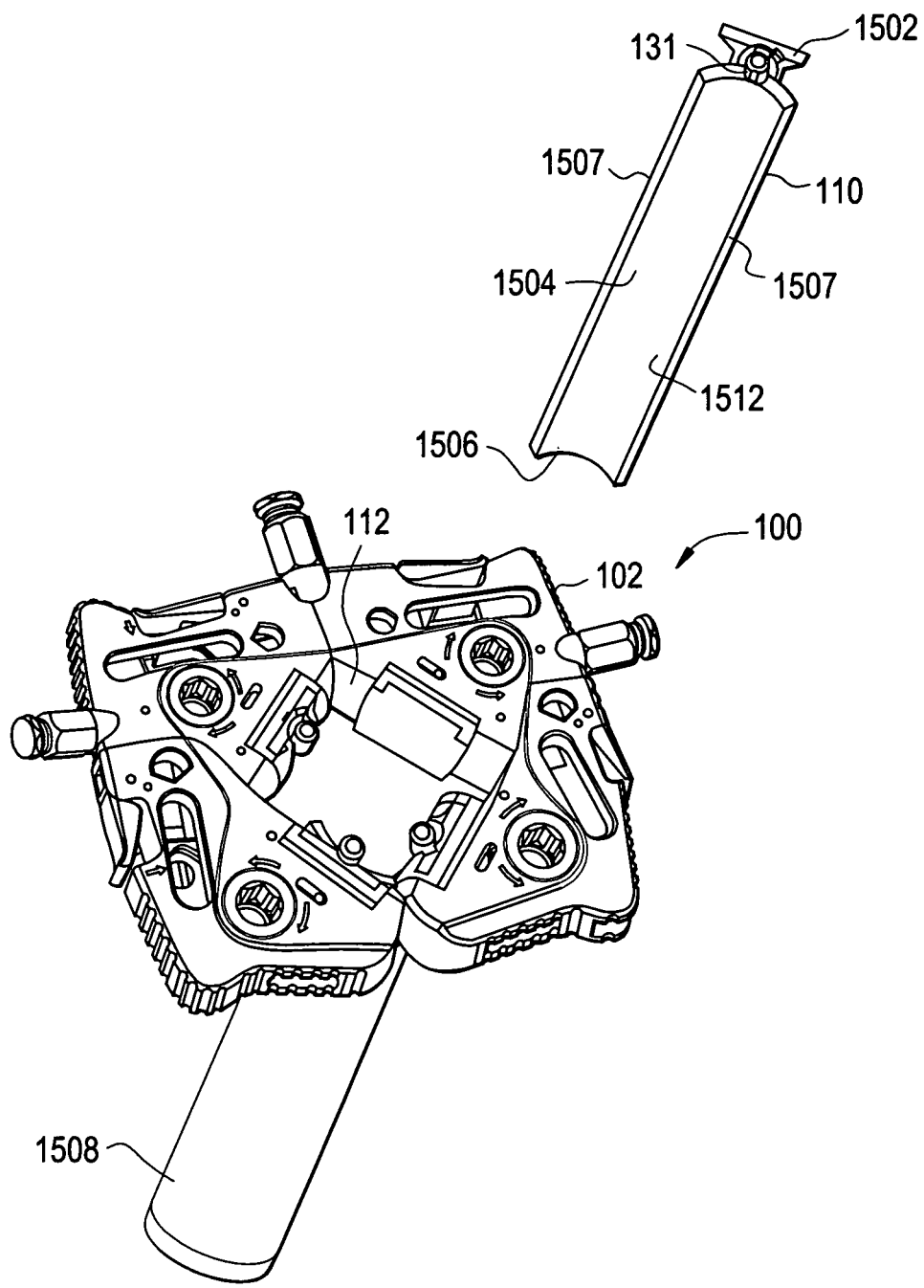
FIG. 15 is a perspective view of an exemplary blade of the retractor shown in FIG. 1.

The blades 110 are configured to be secured to blade holders 112 (*a, b, c, d*) using bolts 131 (*a, b, c, d*), respectively. An exemplary blade 110 is illustrated in FIG. 15, which is a perspective exploded view of the retractor 100 having one blade 110 removed. The blade 110 includes a top portion 1502, a shaft 1504, and a tip 1506. The blade 110 includes an interior portion 1512 and an exterior portion 1508. The blade 110 is configured to be secured to the blade holder 112 with a bolt 131. The bolt 131 can be any locking mechanism, such as a catch-and-release mechanism, a stopper device, a spring-loaded device, or any other device. In some embodiments, the blade 110 is configured to be inserted from the top of the retractor 110, as shown in FIG. 15. Once the blade 110 is inserted, it can be secured in the holder 112. The interior portions 1512 of the blades 110 are configured to face each other when the blades are inserted into the retractor 100. Whereas, the exterior surfaces 1508 of the blades 110 are configured to face away from each other when the blades are inserted into the retractor 100. The exterior surfaces 1508 are configured to push away the tissue (using shafts 1504) when the blades are inserted into the tissue at a surgical site. In some embodiments, the blades 110 are configured to be curved outwards, as shown in FIG. 15. Such curvature is configured to push away tissue in a radial direction and thereby allowing a greater access to the surgical site. As can be understood by one skilled in the art, other shapes of the blades 110 are possible.

Referring back to FIG. 1, once the blades 110 are secured to the blade holders 112, the blades 110 are configured to form a substantially circular interior 127. As can be understood by one skilled in the art, other shapes of the interior 127 can include oval, polygonal, square, hexagonal, octagonal, ellipsoidal, or any other shape. The shape 127 depends on the curvature of the interior surface 1512 (not shown in FIG. 1). When the retractor 100 is in a collapsed (or detracted) state (as shown in FIG. 1), the blades 110 can be configured to have at least the edges 1507 (shown in FIG. 15) touching each other, as shown in FIG. 1.

Figure 3:
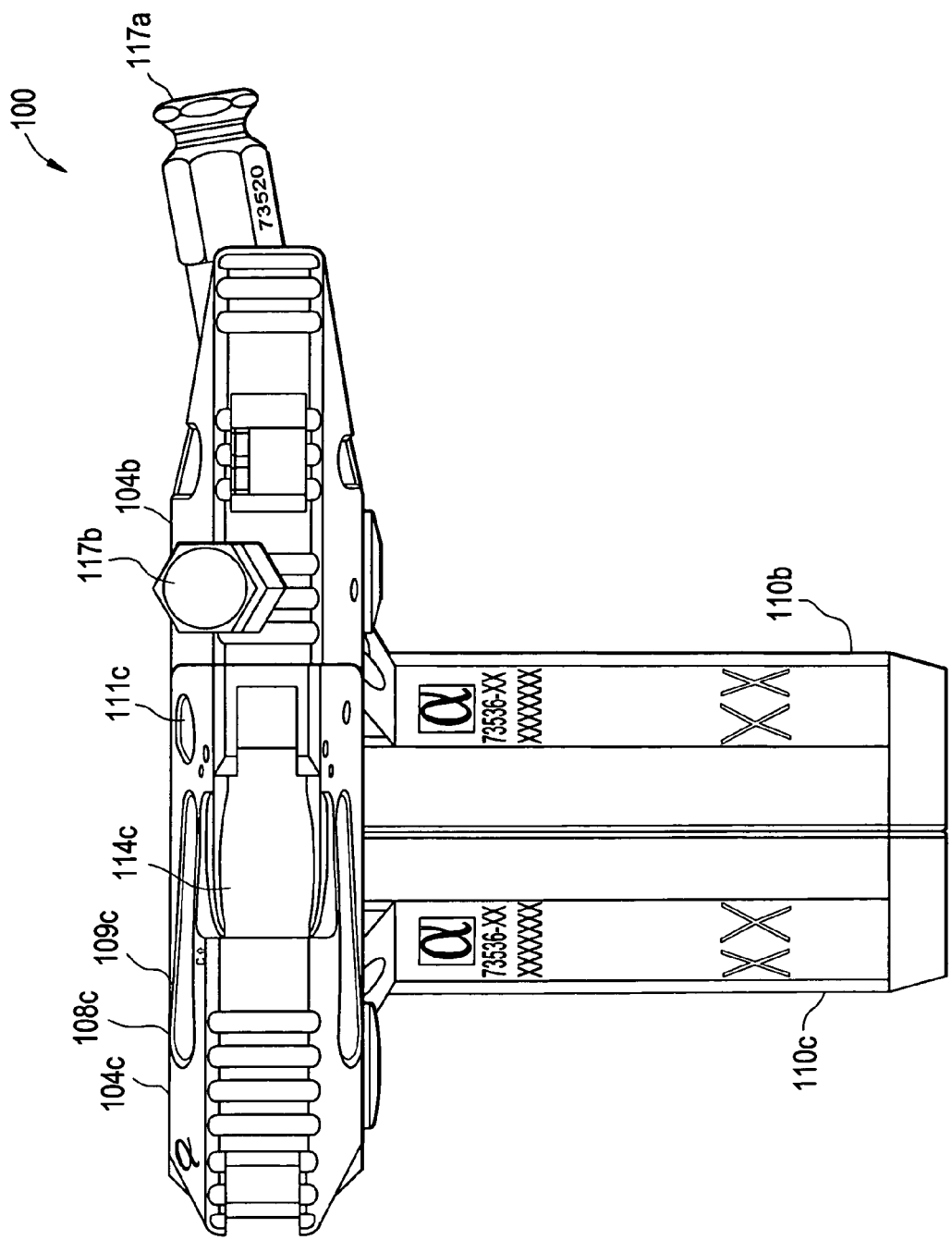
FIG. 3 is a side view of the retractor shown in FIG. 1.

As further illustrated in FIG. 1, the retractor 100 further includes ratchets 114 that are configured to secure position of the quadrants 104 and thereby secure position of the blades 110. The ratchets 114 are disposed substantially adjacent to the detractor assembly 109 and are further configured to partially pivot around pivoting anchors 151 (*a, b, c, d*) in the directions A, B, C, D, respectively. Referring to FIGS. 3 and 7, illustrating side views of the retractor 100 in the collapsed and expanded states, respectively, the ratchet 114c is shown in more detail. FIGS. 3 and 7 further illustrate quadrants 104c and 104b and a ratchet 114c configured to secure quadrant 104c, when the retractor 100 is in the expanded state (FIG. 7). This is accomplished through interaction with railing assemblies disposed within the retractor 100 and illustrated in more detail in FIGS. 4-6.

Figure 5:
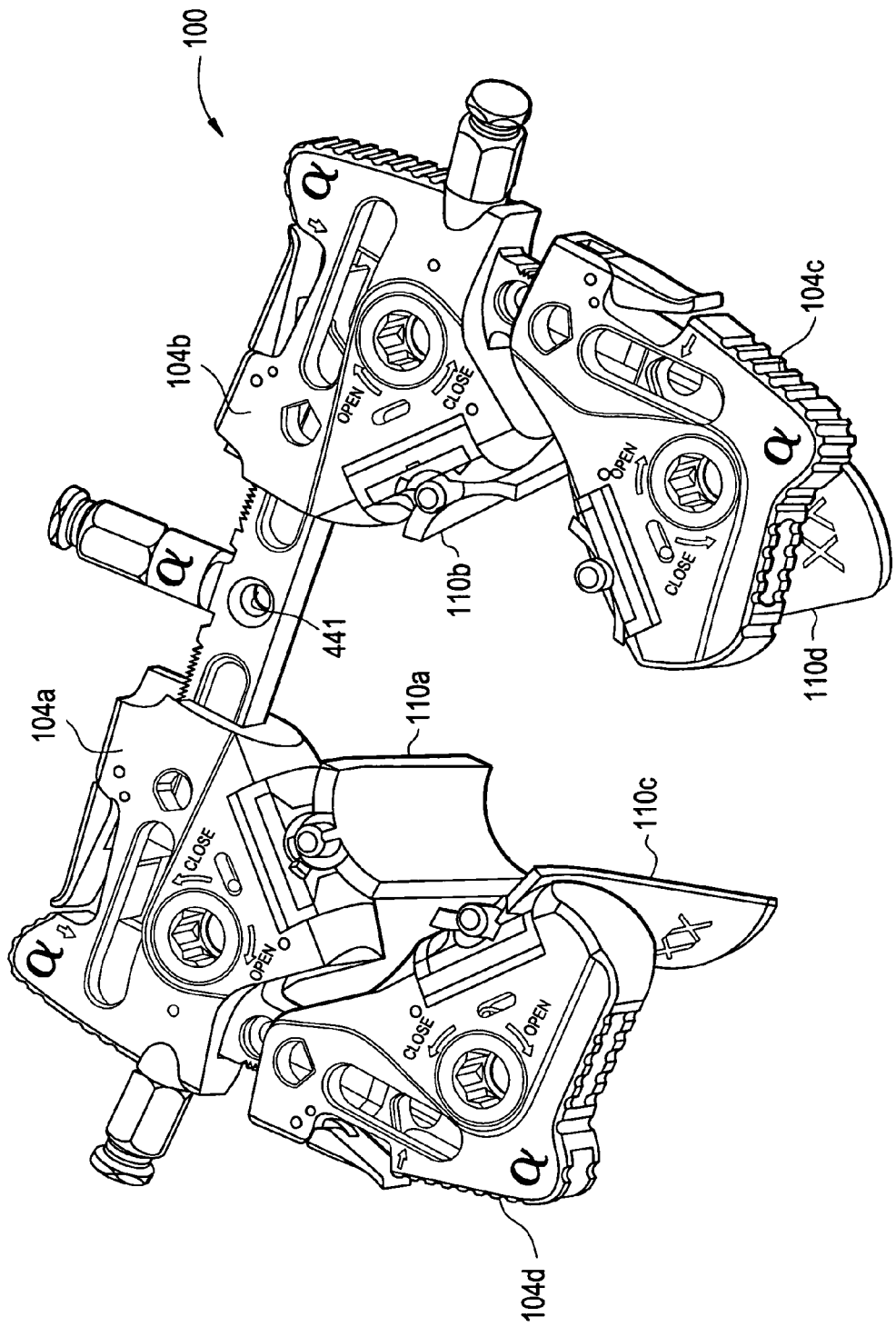
FIG. 5 is another top view of the expanded retractor shown in FIG. 4 illustrating the expanded blades.
Figure 6:
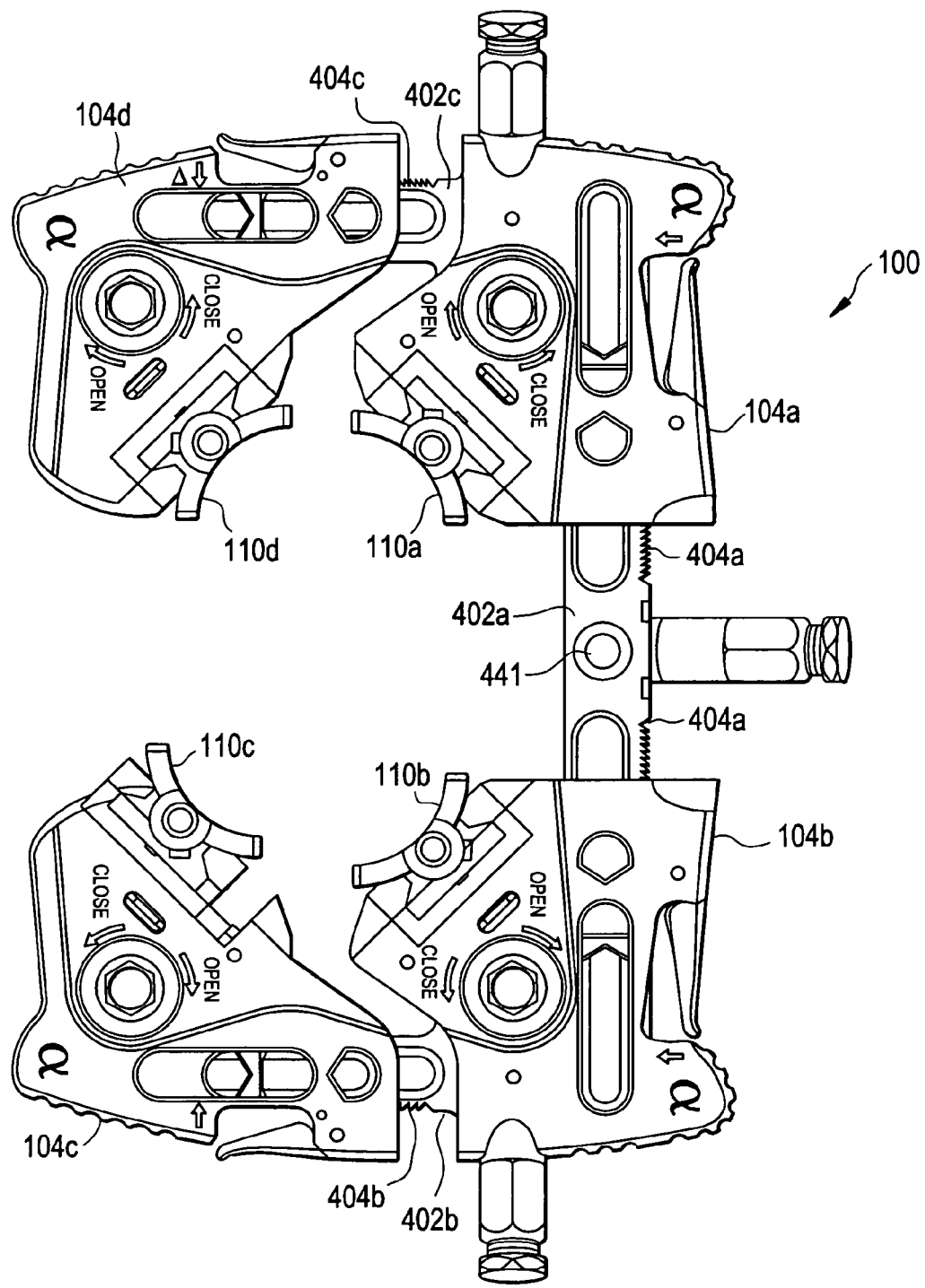
FIG. 6 is a top view of the retractor shown in FIG. 4.
Figure 7:
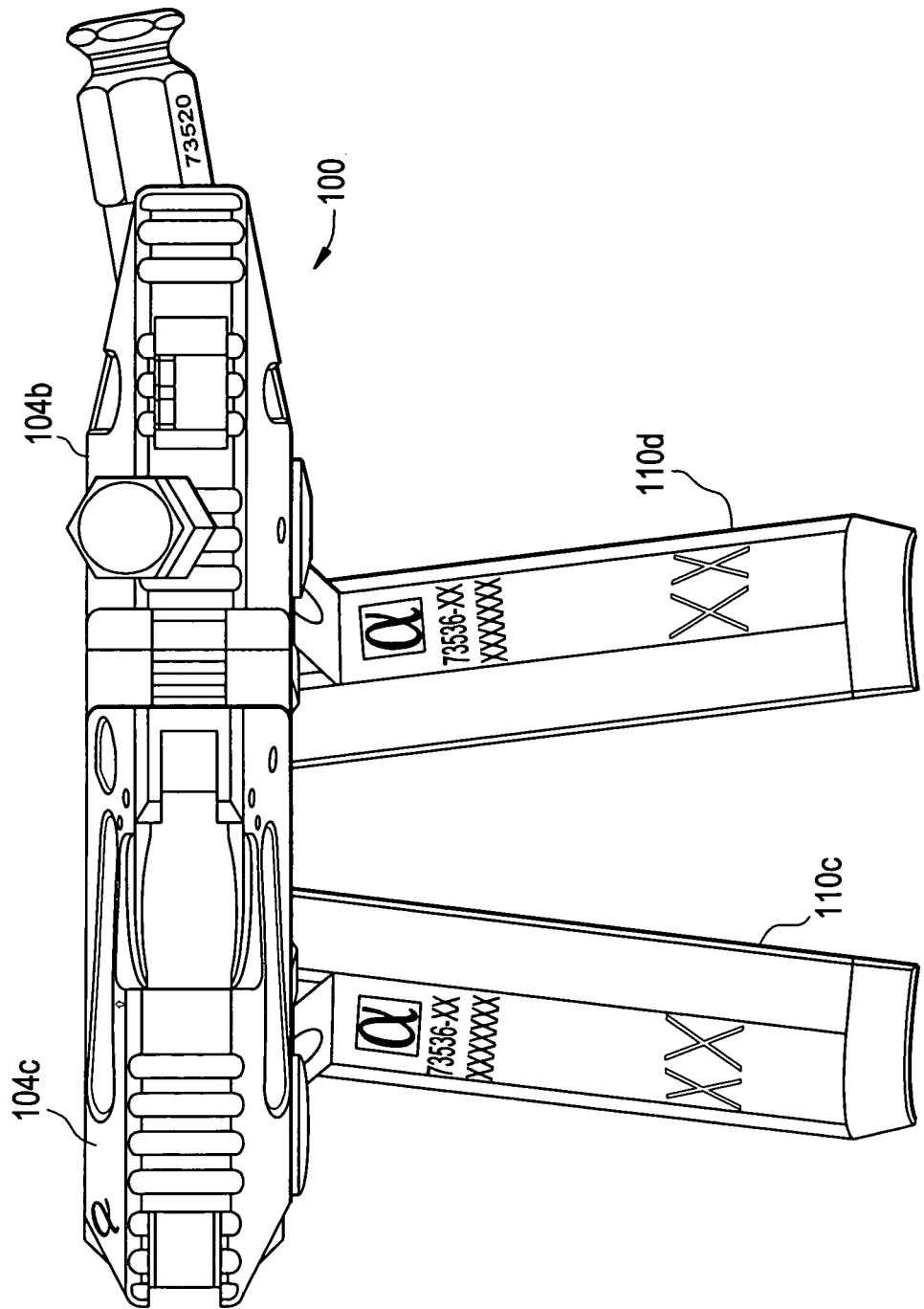
FIG. 7 is a side view of the retractor shown in FIG. 4 illustrating the blades being spread apart using ratchet and gear drive mechanisms.

As shown in FIGS. 4-6 (which are a perspective views (FIGS. 4-5) and a top view (FIG. 6) of an expanded retractor), the retractor 100 includes railing platforms 402 (a, b, c). Each railing platform includes ratchet teeth 404 (a, b, c). Quadrants 104a and 104b are configured to be slidably secured to the railing platform 402a using ratchet teeth 404a. Quadrant 104b is configured to be permanently secured to the railing platform 402b and quadrant 104c is configured to be slidably secured to the railing platform 402b using ratchet teeth 404b. Further, quadrant 104a is configured to be permanently secured to the railing platform 402c and quadrant 104d is configured to be slidably secured to the railing platform 402c using ratchet teeth 404c. The ratchet teeth 404 are configured to allow sliding movement of the appropriate quadrants 404. The ratchet teeth 404 are also configured to secure quadrants 104 in place once desired retraction of the quadrant 104 is achieved.

Figure 12:
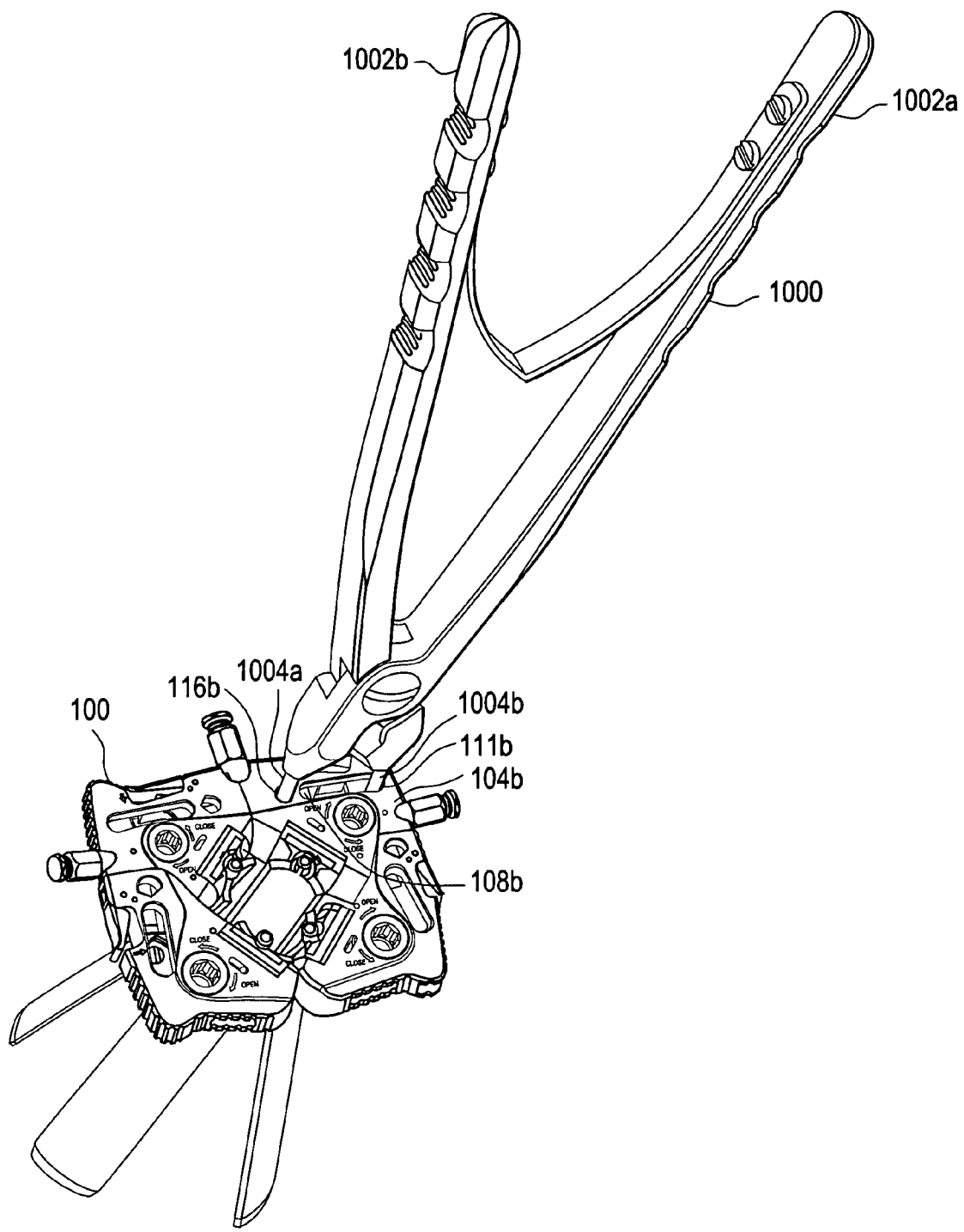
FIG. 12 is a perspective view of the detractor forceps tool shown in FIG. 12 being inserted into the detractor assembly of an unexpanded retractor shown in FIG. 1.
Figure 13:
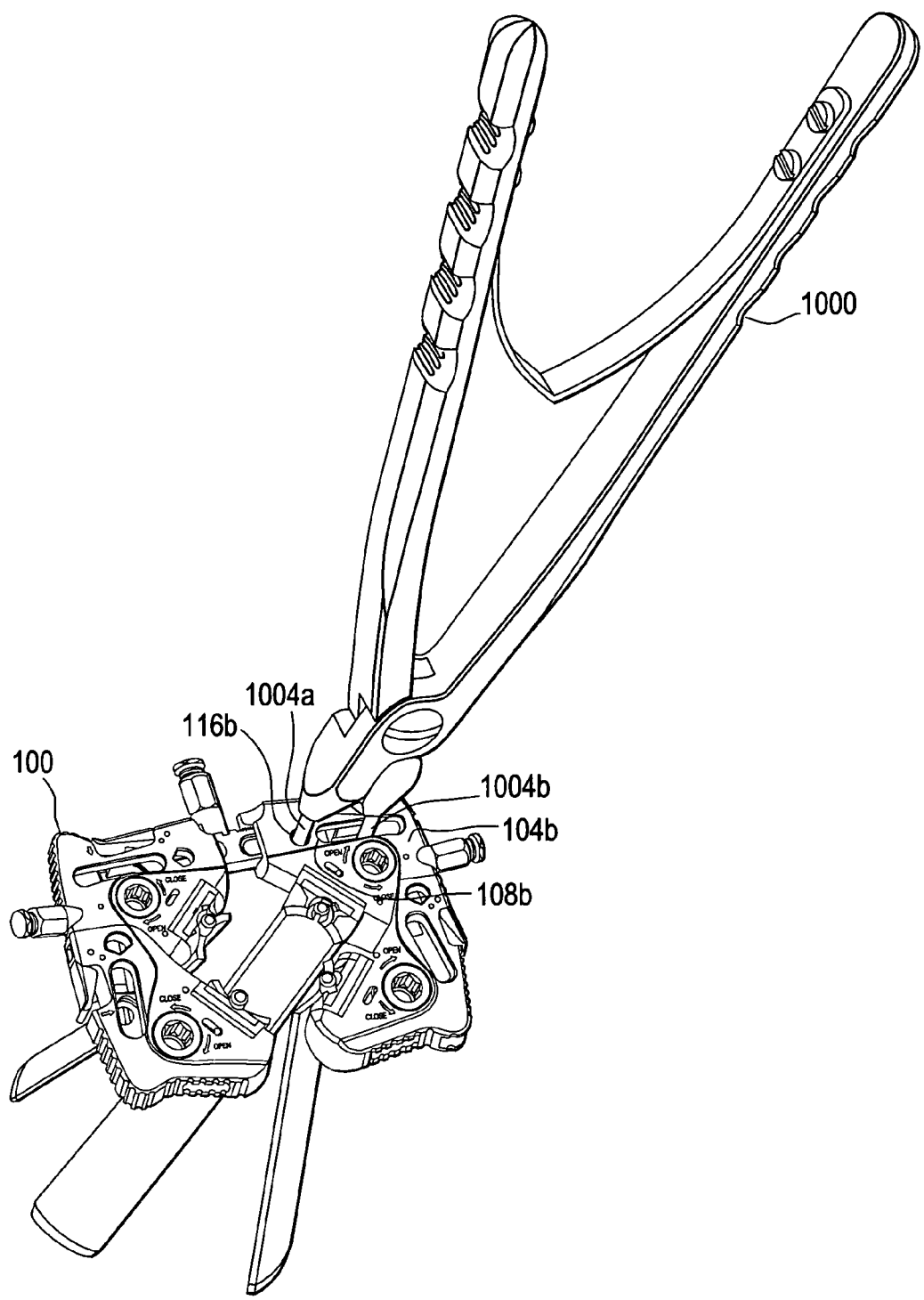
FIG. 13 is a perspective view of the detractor forceps tool shown in FIG. 12 expanding the retractor shown in FIG. 1.
Figure 14:
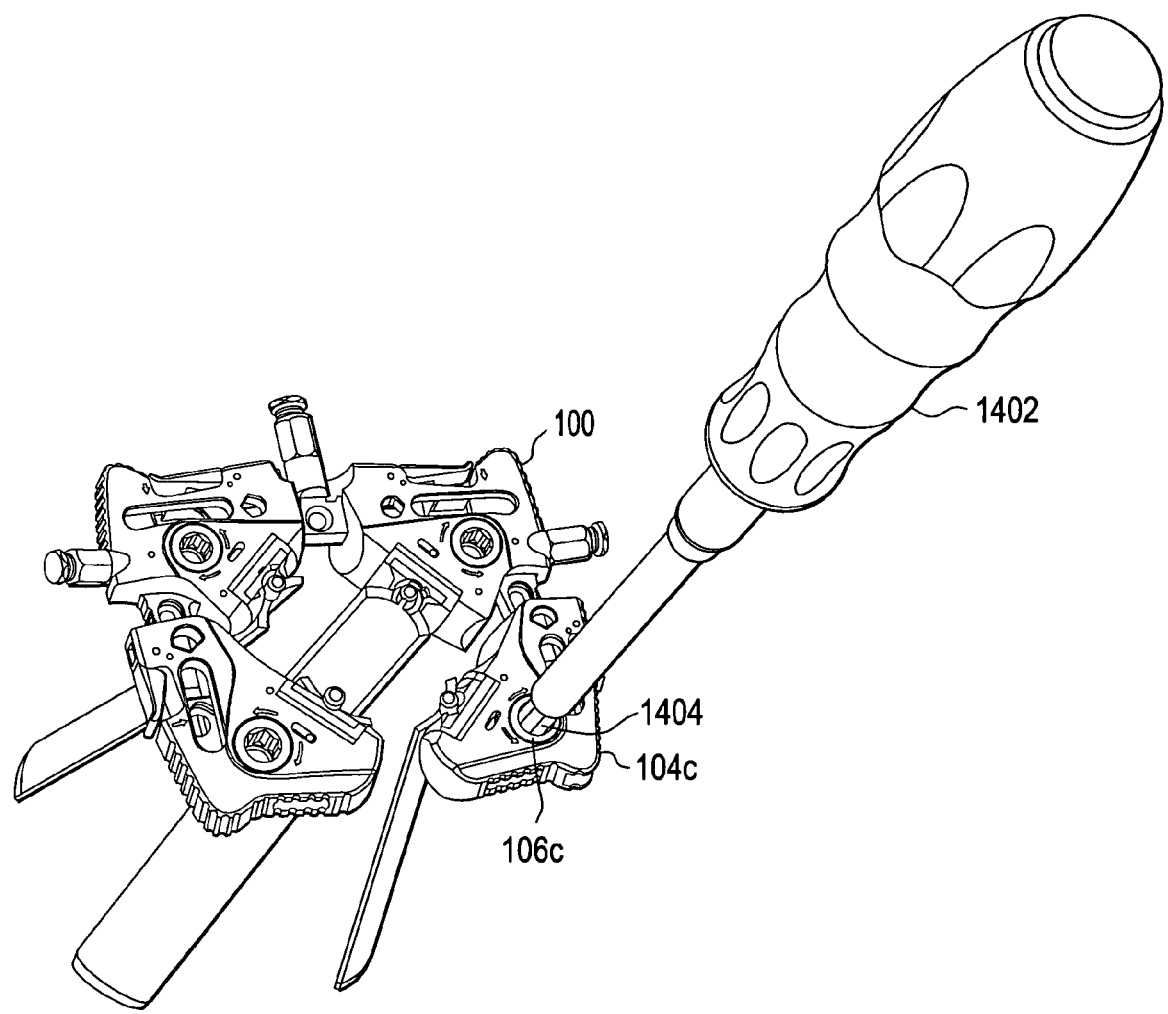
FIG. 14 is a perspective view of an exemplary toeing wrench tool being used to rotate the blades of the retractor shown in FIG. 1.

Such retraction is achieved using a detractor forceps tool 1000, as illustrated in FIGS. 10-13. The tool 1000 is somewhat similar in shape to conventional pliers and includes two handles 1002(a, b) that are joined in the middle 1006 and further include actuating tips 1004(a, b). The tool 1000 can be also configured to include an actuating spring mechanism 1008 that provides resistance to the handles 1002 when they are pushed together in order to pull apart actuating tips 1004. The actuating tips 1004 are configured to be inserted into the detractor assemblies 109. Specifically, the actuating tips 1004 are configured to be inserted into the openings 111 (a, b, c, d) and 116(a, b, c, d). This is illustrated in FIGS. 12-13. FIG. 12 illustrates the tool 1000 being inserted into the assembly 109 with one actuating tip 1004a being inserted into the opening 116b and the other actuating tip 1004b being inserted into the opening 111b. The actuating tips 1004 are configured to fit within the openings 116 and 111. In some embodiments, the actuating tips can be configured to have a square cross-section. Similarly, the openings 116 and 111 are configured to have a square cross-section that is configured to match the cross-section of the actuating tips 1004. In other embodiments, the cross-section of the tips 1004 and openings 116 and 111 can have any other desired shape that is configured to prevent any sliding movement by the tool 1000 once the tool 1000 is engaged with the assembly 109 and the motion of retraction or detraction is performed. FIG. 12 illustrates the tool 1000 being inserted into an unexpanded retractor 100. The handles 1002 of the tool 1000 are spread apart in the unexpanded configuration of the retractor. To expand the retractor 100 (or specific quadrants 104), the handles 1002 are pushed together, thereby pushing the tips 1004 together. This causes openings 111 and 116 to approach each other and further cause translational movement of the quadrant 104 along railing 402. FIG. 13 illustrates the tool 1000 being used to expand (or detract) the retractor 102, i.e., the quadrant 104 has been translated along the railing 402. As shown, the tips 1004 of the tool 100 are being pushed together.

The motions of retraction/detraction are performed by inserting one of the tips 1004 into a stationary opening 116 of the quadrant 104 and the other tip 1004 into a slidable opening 111 of the quadrant 104. Then, the handles 1002 of the tool 1000 are configured to be pushed together, thereby pushing together the tips 1004. This is allowed by the elongated opening 108, i.e., the tip 1004 that is inserted into the slidable opening 111 is configured to move within the opening 108 to and from the stationary opening 116. The ratchet teeth 404 (illustrated in FIG. 4) are configured to allow measured movement as well as locking of the quadrant 104 to a particular desired position. Further, in order for a user to expand the retractor 102 (or a particular quadrant 104 of the retractor 102), the tool 1000, having its handles 1002 at least partially pushed together, is inserted into appropriate openings 111 and 116, then the handles 1002 are further pushed together, thereby translating the quadrants 104 along railings 402 (illustrated in FIG. 4) forcing the blades 110 to be pulled away from the center 120 of the retractor 102 (shown in FIG. 1). To collapse the retractor 102 (or a particular quadrant 104 of the retractor 102), the user can rotate the ratchet 114 toward the quadrant, thereby allowing translation motion of the quadrants 104 along railings 402 forcing the blades 110 to be pushed towards the center 120 of the retractor 102 (shown in FIG. 1).

Figure 16A:
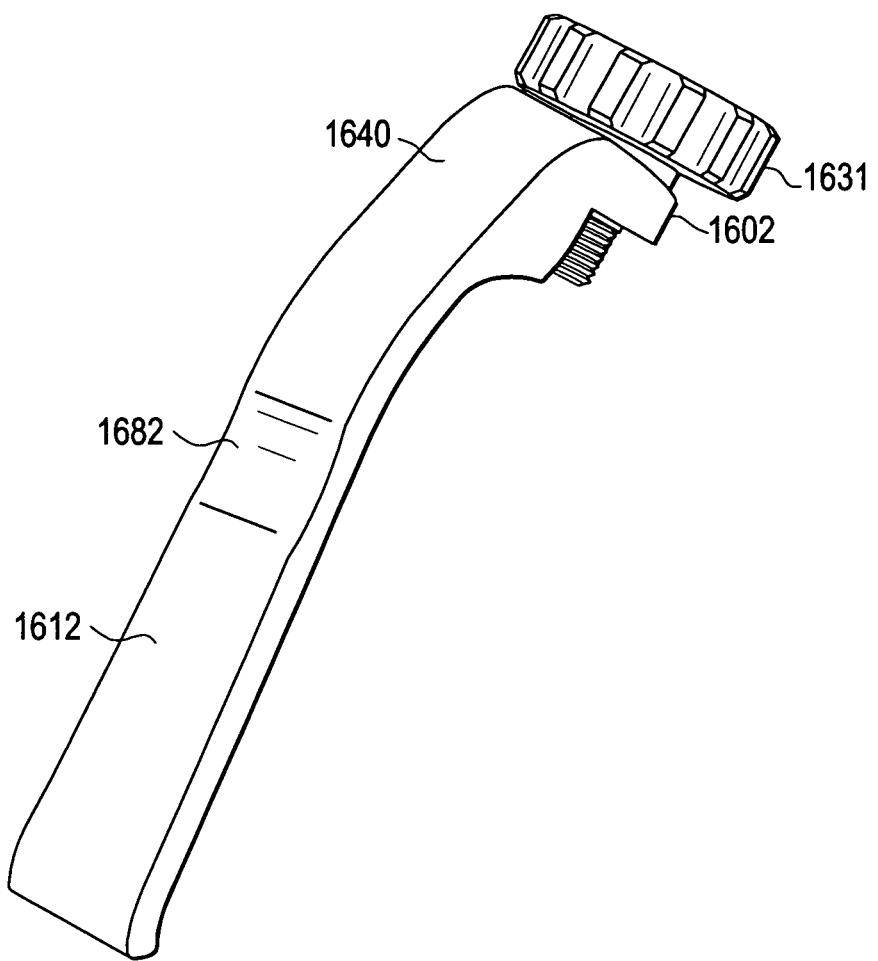
FIGS. 16A-C are perspective views of an exemplary accessory blade for the retractor shown in FIG. 1.
Figure 16B:
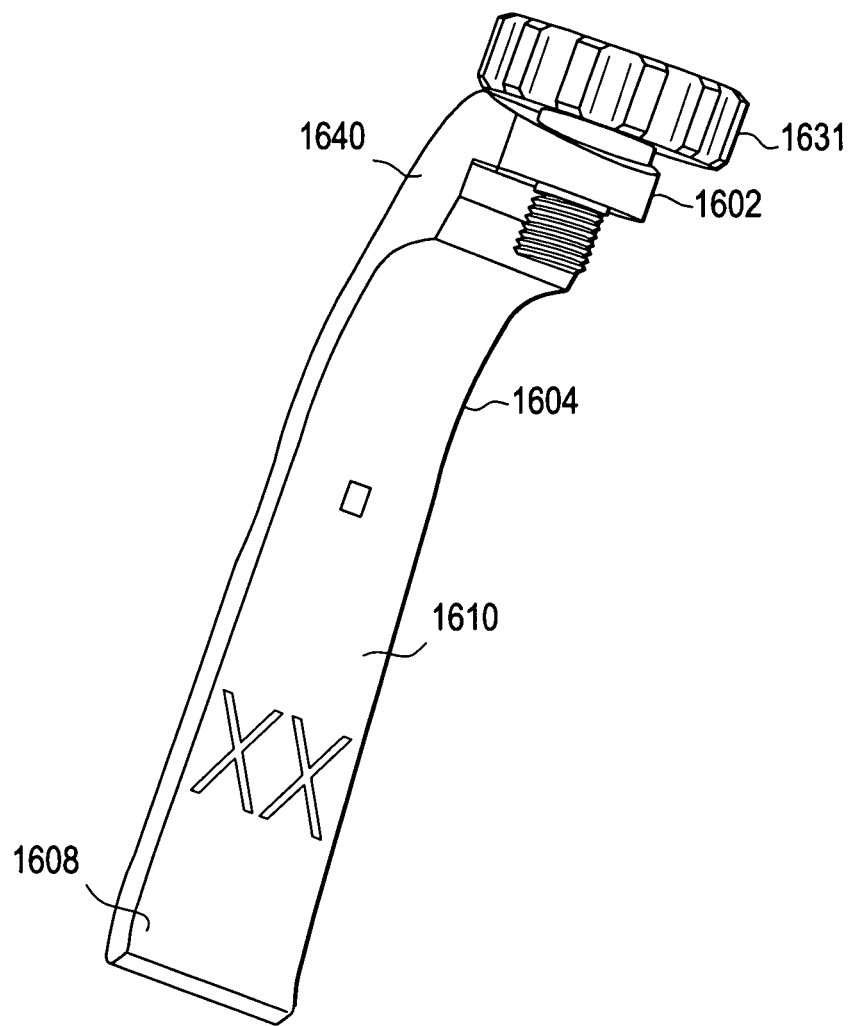
Figure 16C:
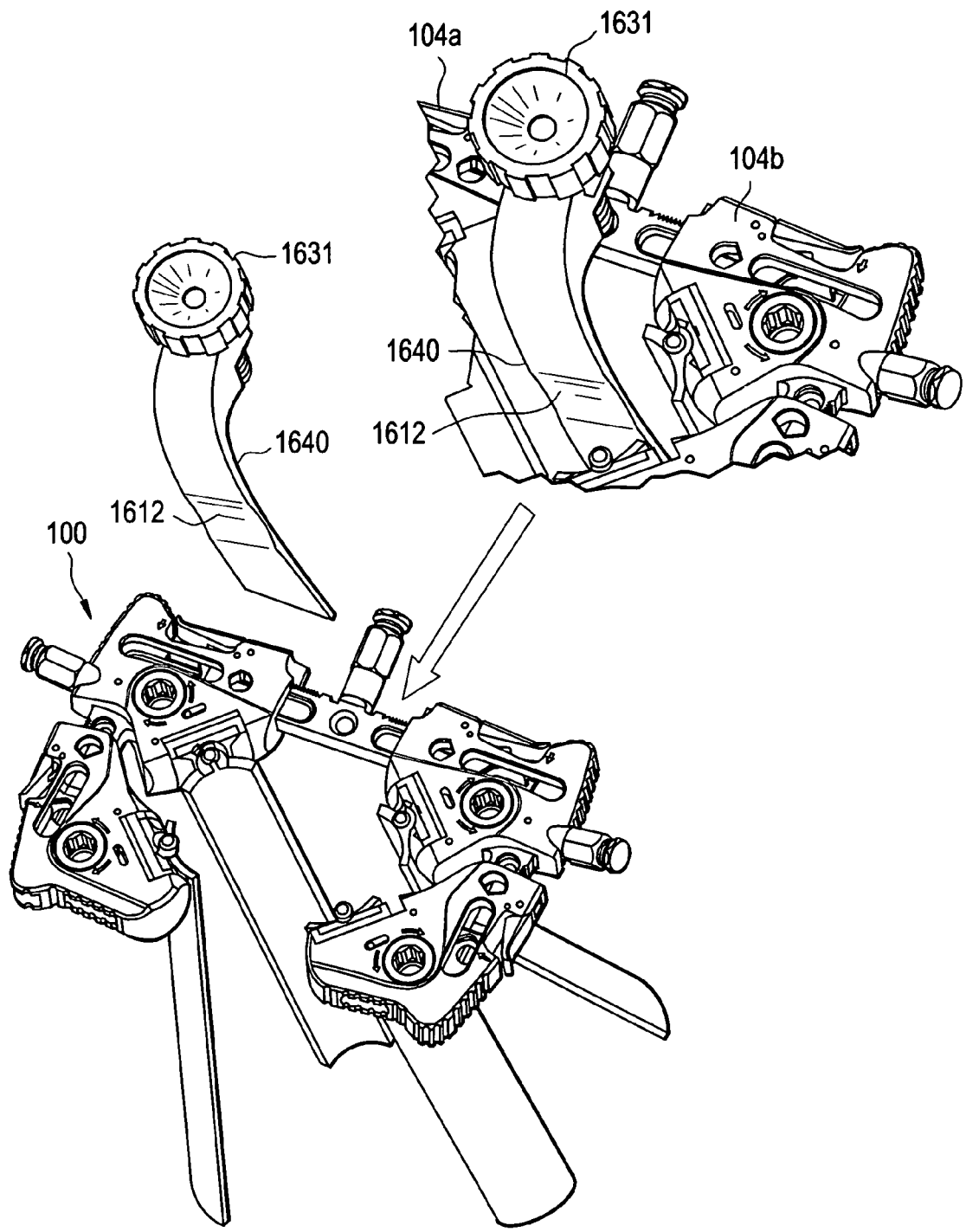

FIGS. 4-6 further illustrate that the railing platform 402a includes an opening 441 configured to accommodate placement of an accessory blade (not shown in FIGS. 4-6). FIGS. 16A-16C illustrate an exemplary accessory blade 1640 configured to be secured to the opening 441 and further configured to further prevent tissue from encroaching on the surgical site. As can be understood by one skilled in the art, the blade 1640 can be attached to any railing 402 of the retractor 100.

Referring to FIGS. 16A-16C, the blade 1640 includes an interior surface 1610 and an exterior surface 1612. The top portion 1602 is configured to be secured to the railing 402a using bolt 1631 located at the top portion 1602 (as shown in FIG. 16C, which illustrates a zoomed portion of the attachment of blade 1640 to the railing 402a). The bolt 1631 can include a threading that allows a user to insert the blade 1640 into the opening 441 and then secure the blade 1640 to the railing 402a by screwing in the bolt 1631. As can be understood by one skilled in the art, the bolt 1631 can be any securing mechanism such as an interlocking mechanism, a catch-and-release mechanism, a stopper device, a spring-loaded device, or any other device. The interior surface 1610 of the blade 1640 is configured to face the interior surfaces 1512 (shown in FIG. 15) of the blades 110 when the blades 110 and the accessory blade 1640 are inserted into and secured to the retractor housing 102. The exterior surface 1612 and the exterior surfaces 1508 (shown in FIG. 15) of the blades 110 are configured to face away from each other when the blades 110 and the accessory blade 1640 are inserted into and secured to the retractor housing 102. The exterior surfaces of the blades 110 and 1640 are also configured to interact with and push away the tissue (using the respective shafts 1504 and 1604) when the blades are inserted into the tissue at the surgical site. The tip 1608 of the blade 1640 can be configured to be curved inward toward interior surface 1610 of the blade 1640. This can ease insertion of the blade 1640 into the tissue. Further, the exterior surface 1612 can be configured to include an inwardly curved portion 1682. Portion 1682 can be configured to further secure blade 1640 inside the tissue, prevent slippage of the blade 1640 at the surgical site and prevent further encroachment of the tissue into the surgical site. As can be understood by one skilled in the art, more than one accessory blade can be inserted and secured to the housing 102 of the retractor 100.

Referring back to FIGS. 3 and 7, the ratchet 114c is configured to interact with ratchet teeth 404c and secure the quadrant 104c in a particular position. This is done by retracting the quadrant 104c along the railing 402c (FIG. 4) whereby the quadrant can be auto-locked when the ratchet 114c interacts with a particular tooth (teeth) of the ratchet teeth 404c. To release the quadrant 104c, the ratchet 114c is rotated (toward the quadrant) to unlock the tooth (teeth) of the ratchet teeth 404c. Then, the quadrant 104c can be translated back towards quadrant 104b or away from the quadrant 104b.

Referring back to FIG. 1, each quadrant 104 includes a gear drive 106. The gear drive 106 is configured to allow rotation of the blades 110 in a plane that is substantially perpendicular to the plane of the housing 102 of retractor 100. Such rotation will be also referred as a distal toeing motion. By rotating the blades 110, the tips 1506 (FIG. 15) are configured to be pushed apart from each other, thus, further spreading the tissue that may be encroaching the surgical site.

Figure 8:
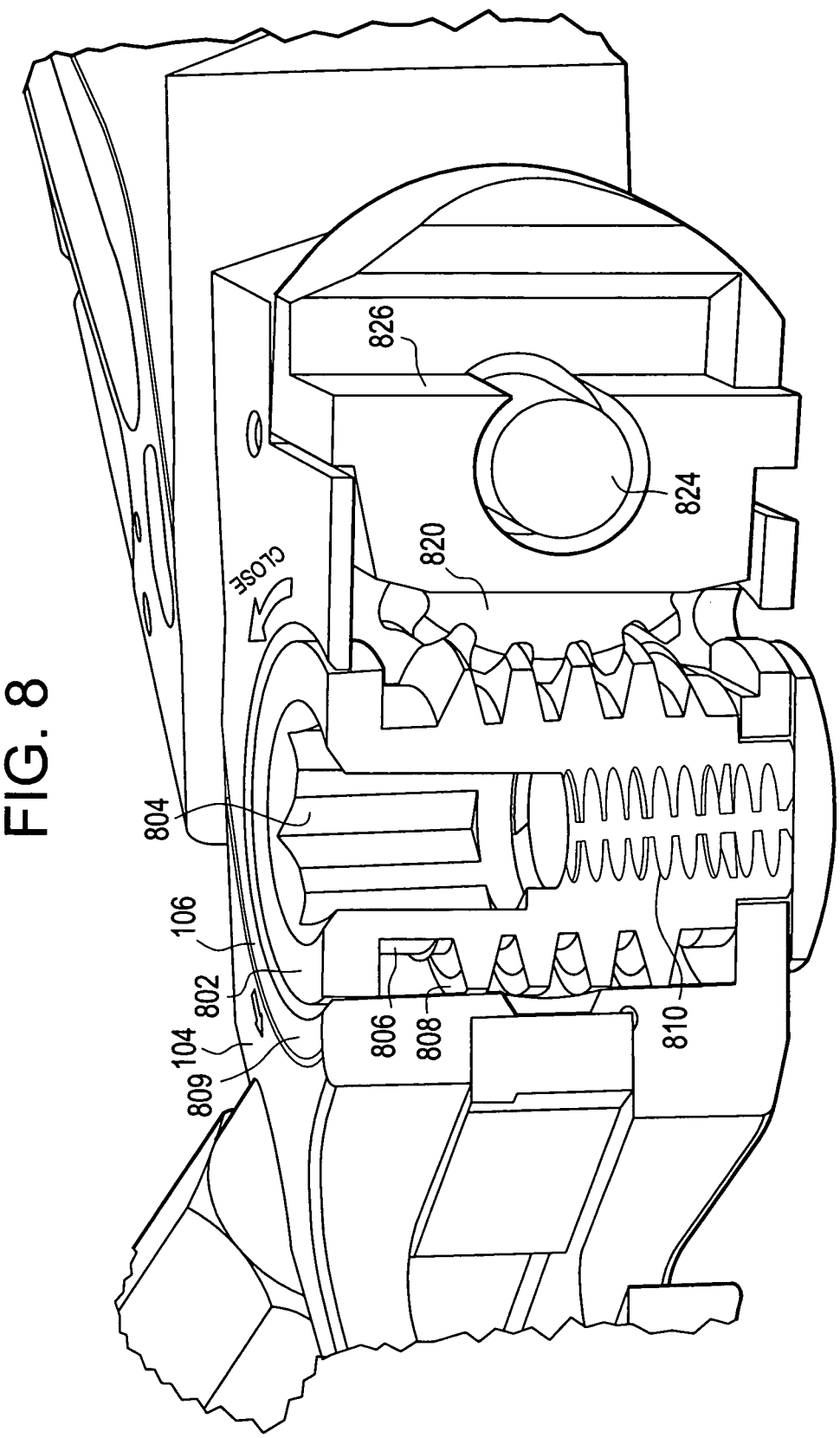
FIG. 8 is a cross-sectional view of a worm gear of the gear drive mechanism of the retractor shown in FIG. 1.
Figure 9:
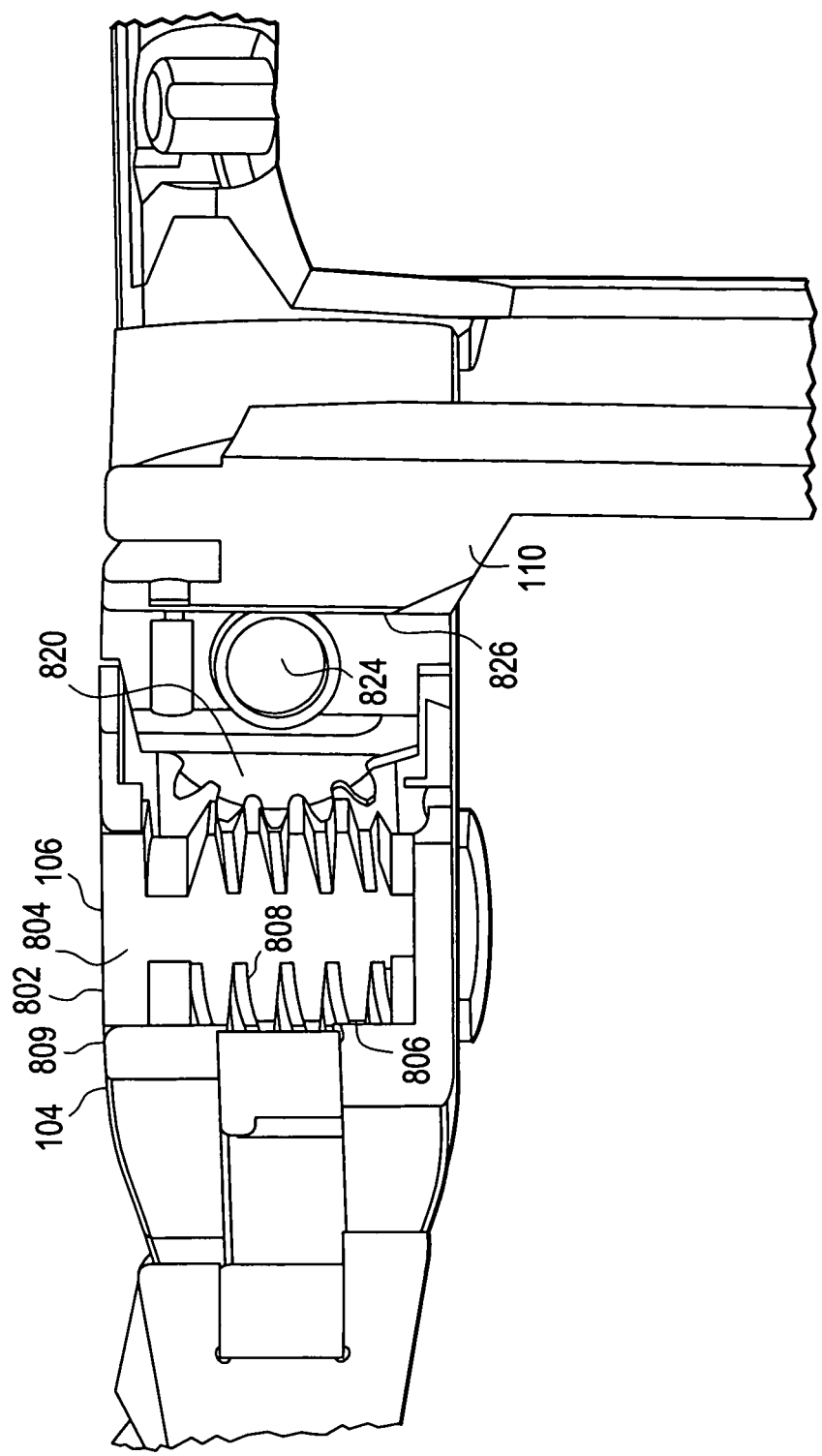
FIG. 9 is another cross-sectional view of the worm gear shown in FIG. 8.
Figure 10:
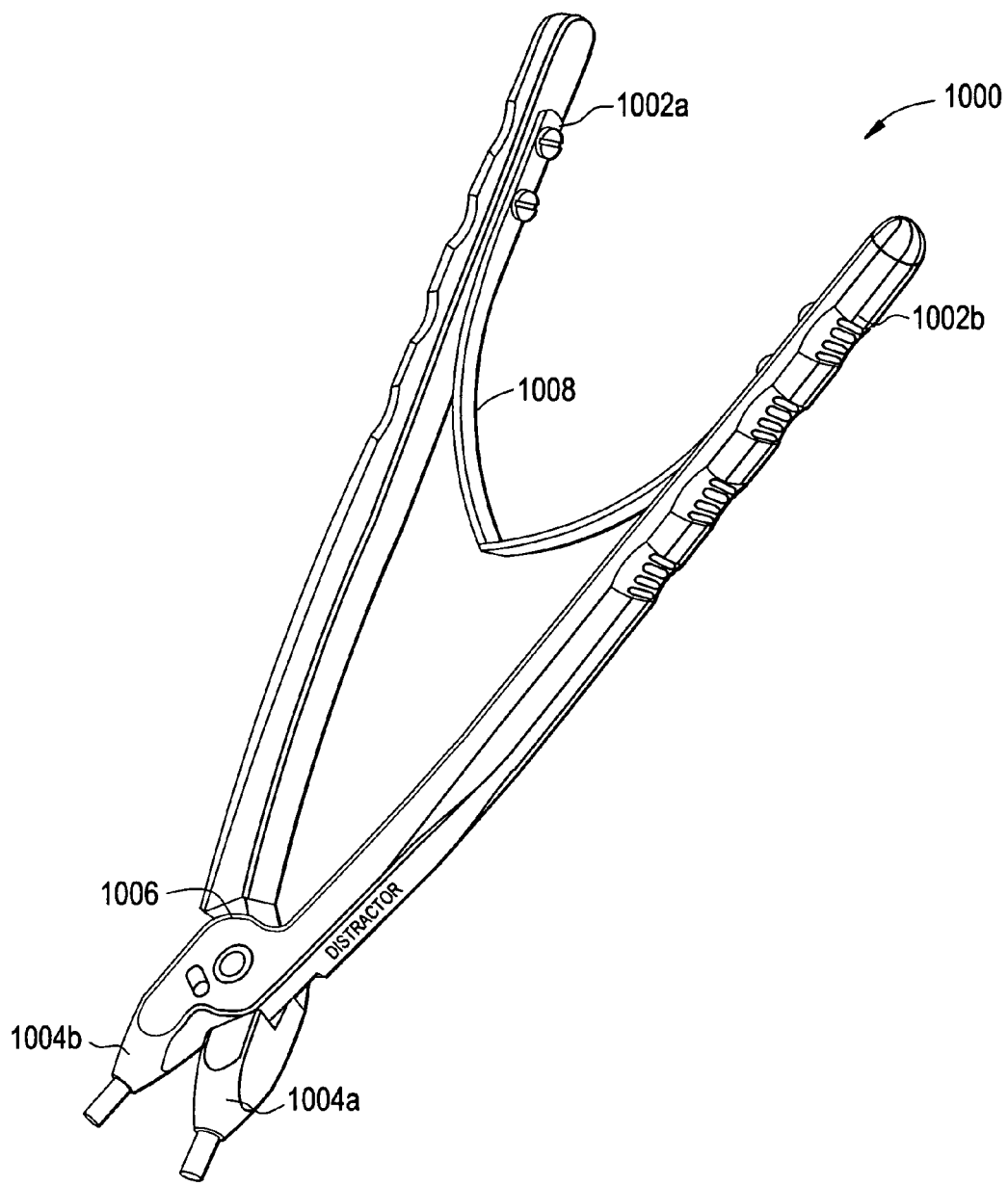
FIG. 10. is a perspective view of an exemplary detractor forceps tool used for expanding retractor shown in FIG. 1.
Figure 11:
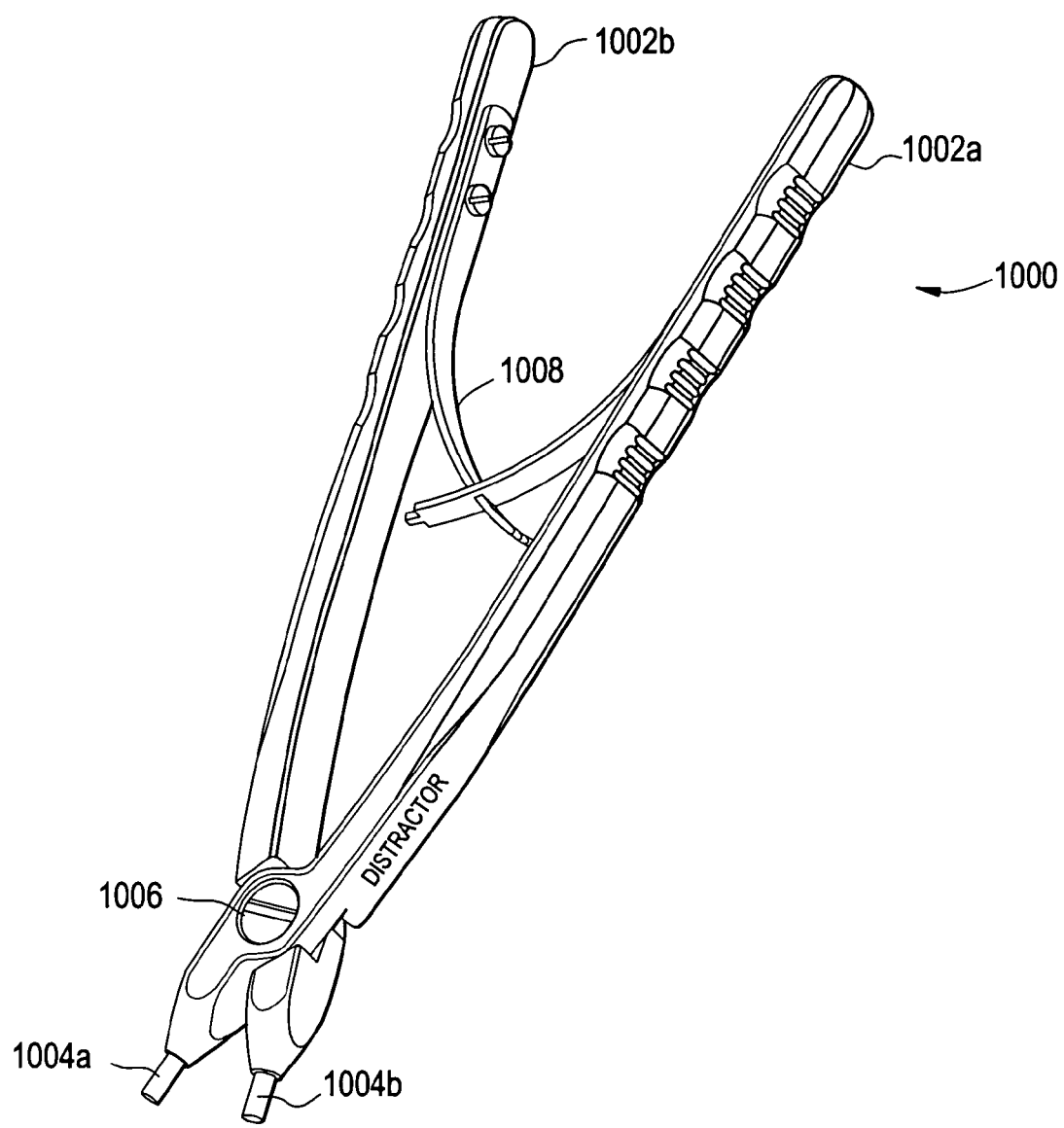
FIG. 11 is another perspective view of an exemplary detractor forceps tool used for expanding retractor shown in FIG. 1.

Referring to FIGS. 1, 8 and 9, the gear drive 106 is illustrated in more detail. The gear drive 106 include a housing 802 having an interior portion 804, an exterior portion 806, threads 808 disposed on the exterior portion 806 in a circular fashion, and a bolt 810. The bolt 810 is configured to retain the gear drive 106 in a casing 809 that is disposed in the quadrant 104 and configured to accommodate placement of the gear drive 106. The interior portion 804 includes polygonal (or any other suitable shape) sides that allow placement of a toeing wrench 1402 (illustrated in FIG. 14). The toeing wrench 1402 includes a top 1404 having polygonal (or any other shape) sides that are configured to substantially match the polygonal sides of the interior portion 804 so as to prevent the wrench 1402 from sliding once it is inserted in the portion 804. The threads 808 on the exterior portion 806 are configured to engage with teeth 822 of a worm wheel 820. The worm wheel 820 is configured to rotate about a pivot rod 824 disposed in the quadrant 104 to secure the worm wheel 820. The worm wheel 820 further includes a flat section 826 disposed opposite the teeth 822 and adjacent the blade 110. The flat section 826 is configured to push blade 110 in either "OPEN" or "CLOSE" direction, as illustrated by respective arrows in FIG. 1. When the blade is rotated in the "OPEN" direction, the tips 1506 of the blade 110 spread apart from each other. When the blade is rotated in the "CLOSE" direction, the tips 1506 of the blade 110 are pushed closer together. The rotation is achieved by inserting the toeing wrench tool 1402 into the interior portion 804 and rotating the tool 1402 in either "CLOSE" or "OPEN" direction. Such rotation of the wrench 1402 causes rotation of the housing 802 and further causes rotation of the threads 808. Rotation of the blades 808, in turn, causes rotation of the worm wheel 820 and, therefore, wheel 820, using its flat section 826, pushes the back surface 1508 (shown in FIG. 15) of the blade 110 in a desired direction.

In some embodiments, a mechanism similar to the one discussed with regard to FIGS. 1, 8, 9, and 14 for toeing accessory blade(s) 1640 can be also provided. As can be understood by one skilled in the art, the toeing of accessory blade(s) 1640 can further push the tissue away from the surgical site.

FIG. 17 illustrates a method 1700 for retracting a body tissue within a body of a patient using a retractor 100, illustrated in FIGS. 1-16. In step 1702, the retractor quadrants 104 are pushed together to allow the blades 110 to be pushed together towards the center 121 of the hollow center portion 120. In one embodiment, the step 1702 is performed if retractor 100 is an expanded state, i.e., the blades 110 pulled away from the center 121.

In step 1704, the retractor 100, having blades 110 pushed together towards the center 121, is placed on the patient at a location where bodily tissue needs to be retracted. This location can be any location on or within the body, such as a location where a surgical procedure is being or will be performed. In an embodiment, the retractor can be used to expose spinal structures during spinal surgery. This allows for minimal disruption of spinal muscles and sensitive elements of the posterior, lateral, and anterior regions of the spine. The retractor 100 can also be used in the thoracolumbar region, as well as, sacral and cervical regions of the spine, or any other regions.

In step 1706, the tool 1000 can be used to selectively translate the quadrants 104 and thereby translating the blades 110 away from the center 121 of the hollow interior 120. The quadrants 104 can be translated the same distance away from the center or different distances away from the center. This translational motion of each quadrant can be performed simultaneously or at different times. As stated above with regard to FIGS. 10-14, the motion is accomplished by squeezing the handles 1002 of the tool 1000. Once the quadrants 104 and the blades 110 are translated to a desired position inside the tissue, toeing wrench tool 1402 can be used to rotate (or "distal toe") the blades 110 and to further spread the tissue near the surgical site. The rotation of the blades causes the tips 1506 of the blades 110 to move further away from the center 121. By forcing the blades 110 apart, the engaged bodily tissue is also spread/forced apart, as illustrated in step 1708. As stated above, this exposes the bodily regions on which a surgical procedure may be performed. Also, by spreading the tissue apart, the surgeon (or other qualified professional) can easily move in and out any surgical tools needed for performing the surgical procedure.

As can be understood by one skilled in the art, the retractor 100 and/or any of its components may have any size, shape, length, thickness, height, weight, or any other parameters. Such parameters may be selected by the surgeon (or other qualified professional) for performance of specific procedures. Further, the retractor 100 and/or any of its components may be manufactured from metal, plastic, synthetic material, or other suitable materials, or any combination thereof.

Further, as stated above, the quadrants 104 along with blades 110 can be gradually retracted or translated along the railings 402 to slowly retract the obstructive bodily tissue away from the surgical site. Alternatively, the quadrants 104 along with blades 110 can be instantaneously retracted or translated along the railings 402 to quickly retract such bodily tissue. Further, the blades 110 can be gradually or simultaneously rotated using the toeing wrench 1402. As can be understood by one skilled in the art, the detractor assemblies 109 and the gear mechanisms 106 can include a stepping mechanism (not shown in FIGS. 1-16) in combination that allows gradual retraction of the blades 110. This allows a surgeon (or other qualified professional) to retract the obstructive tissue step by step and prevent any accidental injury to the sensitive bodily tissues.

Some embodiments of the retractor according to the present invention can include one or more of the following exemplary non-limiting parameters:

1) a closed outer blade construct, or the "tube" formed by the four blades when all are completely closed, can be, for example, greater than 25 mm;
2) an inner blade construct internal diameter ("ID") can be, for example, less than 19 mm;
3) blade depths can be, for example, in a range of between 40 and 100 mm;
4) expansion of retractor may be made incrementally, for example, in 1-2 mm increments or in any other desired increments;
5) capability of distal toe, or rotation of the blade, at 10°, 15° or at any other angles; and 6) an overall diameter of the retractor device can be about 65 mm.

In some embodiments, the blade holder 112 can include a dovetail slot for receiving the blade, which allows the blade 110 to be loaded from the top of the retractor 100 without any tools (although a tool may be used to remove the blade from the retractor body). A spring-loaded piston (not shown in FIGS. 1-16C) can be provided to engage the blade and prevent the blade from popping out. In some embodiments, the blades 110 can be removed in-situ. Further, each blade 110 can be replaced with another blade 110 that can be shorter and/or longer.

In some embodiments, the retractor 100 allows for distal toeing of the blades, which is accomplished by turning a gear 106 provided for on the top of the retractor that translates the blade mechanism to a particular toe angle to provide the capability of expanding the surgical site and limiting the surface skin incision. In some embodiments, the distal toeing of the blades 110 can be in the range between −90 and 90°.

In some embodiments, the retractor 100 allows for minimal impingement across its midline. An accessory arm (not shown in FIGS. 1-16C) can be provided for the retractor and allows a port-hole and/or the retractor to be held in position and fixed to the operating table.

In some embodiments, the retractor 100 can be used to expose spinal structures during spinal surgery. Such embodiments, for example, enable minimal disruption of spinal muscles and sensitive elements of the posterior, lateral, and anterior regions of the spine. Further, some embodiments of the invention are capable of performing in the thoracolumbar region, as well as sacral and cervical regions of the spine.

Some embodiments include an open halo structure to form a rigid platform. This open halo may be used to allow instruments to be manipulated from inside to outside of the halo. The halo may include openings for attaching, for example, a rigid arm to secure the halo (and thus the instrument in some embodiments) in place.

In some embodiments, the blades 110 are included in various lengths and configurations, and may also include various features to accommodate different applications for the retractor. The blades 110 can be used to form a closed exposure to the surgical site and can be installed easily while at this position. The blades can be constructed of various materials to aid in radio translucency, strength, flexibility, and integration with anatomy etc.

Even though the illustrated embodiment of the surgical retractor includes four quadrants (or sections), the present invention is not limited to having four quadrants. As can be understood by one skilled in the art, there can be any number of quadrants (or sections) that are configured to retain blades that retract tissue away from the surgical site.

Example embodiments of the methods and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed:

1. A surgical retractor, comprising:
   a housing configured to include a plurality of sections and a plurality of sides, wherein at least one of the sides is completely open at at least one point along at least one of the sides such that two of the sections are completely uncoupled, wherein each section is configured to accommodate placement of at least one blade;
   a blade holding mechanism configured to secure the at least one blade within said housing;
   a translation mechanism configured to provide translation movement of at least one of the sections, wherein the two completely uncoupled sections do not include the translation mechanism therebetween, wherein said translation mechanism further comprises a detractor assembly configured to translate at least one of said plurality of sections; and
   a rotation mechanism comprising a gear drive assembly configured to provide rotation movement of at least one blade,
   said drive gear assembly further comprising:
      an interior portion configured to accommodate placement of a toeing wrench tool to actuate rotation of said gear drive assembly and, thereby rotational motion of said at least one blade;
      a threaded exterior portion having a plurality of threads; and
      a worm wheel having a plurality of teeth configured to interact with said plurality of threads of said threaded exterior portion;
      wherein said worm wheel is further configured to push said at least one blade upon rotation of the toeing wrench tool.

2. The retractor according to claim 1, wherein said detractor assembly includes a plurality of openings configured to accommodate placement of a detractor forceps tool capable of interacting with a railing system secured within said housing and to translate the at least one section.

3. The retractor according to claim 2, wherein said detractor assembly is configured to translate one said section independently of another said section.

4. The retractor according to claim 2, wherein said detractor assembly is configured to simultaneously translate all sections within said housing.

5. The retractor according to claim 2, wherein said detractor assembly is configured to gradually translate said at least one section.

6. The retractor according to claim 2, further comprising a ratchet assembly configured to secure said at least one section subsequent to said section being translated.

7. The retractor according to claim 2, further comprising an accessory blade configured to be secured to said railing system and further configured to prevent encroachment of tissue into a surgical site.

8. The retractor according to claim 1, wherein said gear drive is configured to rotate one said blade independently of another said blade.

9. The retractor according to claim 1, wherein said gear drive is configured to gradually rotate said at least one blade.

10. The retractor according to claim 1, further comprising at least one of a medial blade, a lateral blade, a cephalad blade, and a caudal blade.

11. The retractor according to claim 1, wherein said blades can be removed in-situ.

12. The retractor according to claim 1, wherein said blades are replaceable.

13. The retractor according to claim 1, wherein said rotation of said blades is configured to be between about −90 and about 90°.

14. The retractor according to claim 1, wherein said blades are configured to be loaded from a first side of said housing.

15. The retractor according to claim 1, further comprising a spring-loaded piston configured to engage and retain at least one of said blades.

16. A method for retracting body tissue within a body of a patient using a retractor device having a housing with a center and configured to include a plurality of sections and a plurality of sides, wherein at least one of the sides is completely open at at least one point along at least one of the sides such that two of the sections are completely uncoupled, wherein each section is configured to accommodate placement of at least one blade, a blade holding mechanism configured to secure the at least one blade within said housing, a translation mechanism configured to provide translation movement of at least one of the sections, wherein the two completely uncoupled sections do not include the translation mechanism therebetween, and a rotation mechanism configured to provide rotation movement of at least one blade, the method comprising the steps of:

inserting the blades attached to the sections of the retractor into the body tissue selected for retraction, wherein the blades of the retractor have been previously pushed together;

translating the sections of the retractor to a desired distance, wherein said translating translates the blades away from the center of the housing thereby spreading the body tissue apart;

rotating a gear drive assembly with a threaded exterior portion having a plurality of threads; and a worm wheel having a plurality of teeth configured to interact with said plurality of threads of said threaded exterior portion, wherein said worm wheel is configured to push at least one blade upon rotation of the gear drive assembly; and rotating the blades in a plane substantially perpendicular to the plane of said translating to further push the body tissue apart.

17. A surgical retractor, comprising:

a first section and a second section slidably secured by a first railing platform for translation;

a third section slidably secured to the first section by a second railing platform for translation;

a fourth section slidably secured to the second section by a third railing platform for translation;

a blade holding mechanism configured to secure at least one blade on each of the four sections;

a gear drive assembly configured to provide rotational movement of at least one blade; and an accessory blade holding mechanism on the first railing platform, wherein the third and fourth sections are completely uncoupled without a railing platform for translation therebetween wherein the gear drive assembly comprises:

a drive gear including an interior portion configured to accommodate placement of a toeing wrench tool to actuate rotation of said gear drive assembly and, thereby rotational motion of said at least one blade; and a threaded exterior portion having a plurality of threads; and a worm wheel having a plurality of teeth configured to interact with said plurality of threads of said threaded exterior portion to push said at least one blade upon rotation of the toeing wrench tool.

\* \* \* \* \*